(12) United States Patent
Hong et al.

(10) Patent No.: US 10,689,315 B2
(45) Date of Patent: Jun. 23, 2020

(54) METHOD FOR CO-PRODUCING LOW-CARBON FOAMING AGENTS

(71) Applicant: Zhejiang Quhua Fluor-Chemistry Co Ltd, Zhejiang (CN)

(72) Inventors: Jiangyong Hong, Zhejiang (CN); Bo Yang, Zhejiang (CN); Yang Zhao, Zhejiang (CN); Yan Zhang, Zhejiang (CN); Huadong Zhou, Zhejiang (CN); Hao Ouyang, Zhejiang (CN); Haitao Gong, Zhejiang (CN); Min Fang, Zhejiang (CN)

(73) Assignee: Zhejiang Quhua Fluor-Chemistry Co Ltd, Zhejiang (CN)

( * ) Notice: Subject to any disclaimer, the term of this patent is extended or adjusted under 35 U.S.C. 154(b) by 0 days.

(21) Appl. No.: 16/337,408

(22) PCT Filed: Jun. 25, 2018

(86) PCT No.: PCT/CN2018/000234
§ 371 (c)(1),
(2) Date: Mar. 28, 2019

(87) PCT Pub. No.: WO2019/019557
PCT Pub. Date: Jan. 31, 2019

(65) Prior Publication Data
US 2020/0039902 A1 Feb. 6, 2020

(30) Foreign Application Priority Data

Jul. 24, 2017 (CN) .......................... 2017 1 0604867

(51) Int. Cl.
| | | |
|---|---|---|
| *C07C 17/20* | (2006.01) | |
| *B01J 23/80* | (2006.01) | |
| *B01J 23/825* | (2006.01) | |
| *C07C 17/23* | (2006.01) | |
| *C07C 17/38* | (2006.01) | |
| *C07C 19/08* | (2006.01) | |
| *C07C 21/18* | (2006.01) | |

(52) U.S. Cl.
CPC .............. *C07C 17/206* (2013.01); *B01J 23/80* (2013.01); *B01J 23/825* (2013.01); *C07C 17/23* (2013.01); *C07C 17/38* (2013.01); *C07C 19/08* (2013.01); *C07C 21/18* (2013.01)

(58) Field of Classification Search
CPC ....... C07C 17/20; C07C 17/38; C07C 17/206; C07C 17/205; C07C 17/383; C07C 21/04; C07C 21/18; B01J 23/26; B01J 35/0006; B01J 2253/33; B01J 2523/27
See application file for complete search history.

(56) References Cited

U.S. PATENT DOCUMENTS

| | | | |
|---|---|---|---|
| 5,710,352 A | 1/1998 | Tung | |
| 6,077,982 A | 6/2000 | Yates et al. | |
| 2015/0224470 A1* | 8/2015 | Tung .................... | C07C 17/206 422/187 |
| 2019/0047925 A1* | 2/2019 | Hong ...................... | B01J 23/26 |

FOREIGN PATENT DOCUMENTS

| | | |
|---|---|---|
| CN | 102164881 | 8/2011 |
| CN | 102361842 | 6/2015 |
| CN | 103189339 | 1/2016 |
| CN | 106278810 | 1/2017 |
| CN | 106349005 | 1/2017 |
| CN | 107324968 | 11/2017 |

OTHER PUBLICATIONS

"International Search Report (Form PCT/ISA/210)", dated Sep. 27, 2018, with English translation thereof, pp. 1-4.

* cited by examiner

*Primary Examiner* — Jafar F Parsa
(74) *Attorney, Agent, or Firm* — JCIPRNET

(57) ABSTRACT

The invention discloses a method for co-operating low-carbon foaming agents, comprising: preheating 1,1,1,3,3-pentachloropropane and hydrogen fluoride and then introducing into a reactor to have a reaction in the presence of a catalyst to obtain a reaction product, and separating and purifying to obtain the following low-carbon foaming agent products: trans-1,3,3,3-tetrafluoropropene, cis-1,3,3,3-tetrafluoropropene, 1,1,1,3,3-pentafluoropropane, trans-1-chloro-3,3,3-trifluoropropene, cis-1-chloro-3,3,3-trifluoropropene. The invention has the advantages of simple process, environmental friendliness, high production efficiency and low cost.

6 Claims, 1 Drawing Sheet

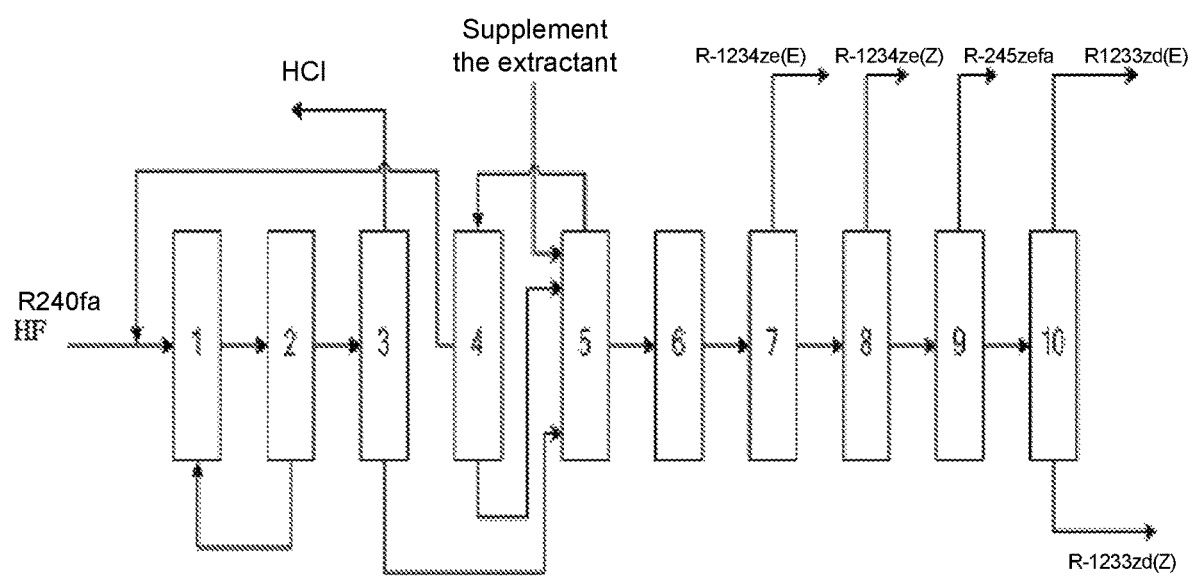

METHOD FOR CO-PRODUCING LOW-CARBON FOAMING AGENTS

CROSS-REFERENCE TO RELATED APPLICATION

This application is a 371 of international application of PCT application serial no. PCT/CN2018/000234, filed on Jun. 25, 2018, which claims the priority benefit of China application no. 201710604867.1, filed on Jul. 24, 2017. The entirety of each of the above-mentioned patent applications is hereby incorporated by reference herein and made a part of this specification.

BACKGROUND OF THE INVENTION

1. Technical Field

The invention relates to the technical field of low-carbon foaming agents, in particular to a method for co-producing low-carbon foaming agents.

2. Background Art

HCFC-based and HFC-based chemicals have been widely used in many different applications in the industry, particularly as refrigerants, aerosol propellants, foaming agents and solvents. However, the ozone depleting potential (ODP) of most of HCFCs and the global warming potential (GWP) of HFCs are very serious. As a result, more environmentally friendly alternatives have been introduced to replace HCFCs and HFCs. Trans-1-chloro-3,3,3-trifluoropropene (R-1233zd(E)), trans-1,3,3,3-tetrafluoropropene (R-1234ze (E)) and 1,1,1,4,4,4-hexafluoropropylene (R-1336mzz (Z)), etc. are currently the most promising low-carbon foaming agents, which are widely used in thermal insulation materials of refrigeration equipment, such as refrigerators, freezers, water dispensers, automotive air conditioners, central air conditioners, refrigerating houses, commercial refrigeration, ice water machine, ice cream machine, and freezing condensing unit, and also can be used in refrigerants, aerosol propellants, medical aerosols, insecticide propellants, and magnesium alloy shielding gas, etc.

A low-carbon foaming agent is generally prepared from a chloroalkene or a chlorohydrocarbon and anhydrous hydrogen fluoride in the presence of a fluorination catalyst. The reacted material enters a HCl column to separate HCl, and then enters a phase separator to separate hydrogen fluoride and organics, and the separated HF is returned to a reactor for recycling. After the phase separation, hydrofluoric acid in the organic phase further recovers hydrogen fluoride by azeotropic distillation. Since the crude organic product and the hydrogen fluoride have a certain azeotropy, the organic crude product still contains a small amount of unseparated HCl and HF, the unseparated HCl and HF also need to enter the water/alkali washing system together with the crude organic product to be absorbed to generate a large amount of spent acid, and a gas phase product from the water/alkali washing system is dried and rectified to obtain a low-carbon foaming agent product. It can be seen that a large amount of useless spent acid containing HCl and HF is generated in the production of low-carbon foaming agents.

An example is Chinese Patent CN102361842B for an invention entitled "Separation of R-1233zd(E) from Hydrogen Fluoride, published on Jun. 3, 2015, and the invention relates to a method for separating R-1233zd(E) from an azeotropic mixture or azeotrope-like mixture of R-1233zd (E) and HF. The method employs cold liquid phase separation and multiple azeotropic distillation systems. However, the invention has the following disadvantages: (1) since the reaction uses a liquid phase to catalyze fluorination, the reaction liquid is coked and carbonized, the catalyst is easily deactivated, and once the catalyst is deactivated, the treatment of the catalyst has great environmental problems; (2) a phase separator required for cold liquid phase separation is large, and when there is a large amount of HF, the phase separator is a major hazard source, causing a large safety risk.

Another example is Chinese Patent CN103189339B for an invention entitled "Continuous Low-temperature Process to Produce Trans-1-chloro-3,3,3-trifluoropropene (R-1233zd(E)), published on Jan. 20, 2016, and the invention discloses a process for producing R-1233zd(E) by carrying out a continuous reaction without using a catalyst. An integrated system for producing hydrofluoroolefins, particularly R-1233zd(E), is also disclosed. The production process consists of six main unit operations: (1) fluorinating 1,1,1,3,3-pentachloropropane (R-240fa) using HF (in a continuous or semi-batch manner) and taking out a by-product HCl and a product R-1233zd(E) simultaneously; (2) recycling unreacted R-240fa and HF together with the underfluorinated by-product back to (1); (3) separating and purifying the by-product HCl; (4) separating excessive HF and returning the excessive HF to (1); (5) purifying the final product R-1233zd(E); and (6) isomerizing the by-product cis-1-chloro-3,3,3-trifluoropropene (R-1233zd(Z)) to R-1233zd(E) to maximize the process yield. However, the invention has the following disadvantages: (1) The reaction part involves a liquid phase reaction, and since the reaction rate is slow without the addition of a catalyst, more reactors are required, many complicated instruments and control valves are required in industrialization, the reactor size is large, the production capacity is small, and the energy consumption is too large. (2) sulfuric acid is used for recovering HF, the treatment of waste sulfuric acid is difficult, and the production process causes environmental issues to some degree; (3) the invention produces a single product and only produces R-1233zd(E), and the produced R-1233zd(E) only can be isomerized to R-1233zd(E) with an additional reactor.

A further example is U.S. Pat. No. 6,077,982 for an invention entitled "Purification of 1,1,1,3,3-pentafluoropropane (R-245fa), published on Jul. 20, 2000, and the invention discloses a method for removing R-1233zd in R-245fa by adding chlorine gas for reaction. The purification problem of R-245fa is solved, but this method wastes a lot of R-1233zd, and produces a lot of high-boiling residues, causing more serious problems in three wastes treatment.

SUMMARY OF THE INVENTION

The invention overcomes the defects of the prior art and provides a method for co-producing low-carbon foaming agents with simple process, environmental friendliness, high production efficiency and low cost.

In order to solve the above technical problem, the technical solution adopted by the invention is: a method for co-producing low-carbon foaming agents, comprising the following steps:

(1) preheating 1,1,1,3,3-pentachloropropane and hydrogen fluoride, introducing into a reactor, and reacting in the presence of a catalyst to obtain a reaction product, wherein the ratio of 1,1,1,3,3-pentachloropropane and hydrogen fluoride is 1:10-40, the reaction temperature is 150-400° C., the reaction pressure is 0.1-2.0 MPa, and the material space velocity is 10-1000 h$^{-1}$;

(2) introducing the reaction product obtained in Step (1) into a recycle column to obtain a recycle column overhead fraction and a recycle column bottom component;

(3) introducing the recycle column overhead fraction obtained in Step (2) into a hydrogen chloride separation column to obtain a hydrogen chloride separation column overhead fraction and a hydrogen chloride separation column bottom component;

(4) introducing the hydrogen chloride separation column bottom component obtained in Step (3) and an extractant into an extraction column for extraction to obtain an extraction column overhead component and an extraction column bottom component; and (5) alkaline washing the extract column bottom component obtained in Step (4) and then rectifying to obtain the following low-carbon foaming agent products: trans-1,3,3,3-tetrafluoropropene (R-1234ze)(E)), cis-1,3,3,3-tetrafluoropropene (R-1234ze(Z)), 1,1,1,3,3-pentafluoropropane (R-245 fa), trans-1-chloro-3,3,3-trifluoropropene (R-1233zd (E)), and cis-1-chloro-3,3,3-trifluoropropene (R-1233zd (Z)).

As a preferred embodiment of the invention, in Step (1) the catalyst is preferably $Cr_2O_3$/In or $Cr_2O_3$/Zn.

As a preferred embodiment of the invention, the load of In in the catalyst $Cr_2O_3$/In or $Cr_2O_3$/Zn is preferably 1-10 wt % (mass percentage), and the load of Zn in the catalyst $Cr_2O_3$/In or $Cr_2O_3$/Zn is preferably 1-10 wt %.

As a preferred embodiment of the invention, the recycle column bottom component in Step (2) can be recycled to the reactor.

As a preferred embodiment of the invention, in Step (4) the extraction column overhead component can be introduced into a hydrogen fluoride recovery column for separation to obtain an overhead fraction and a bottom component, the overhead fraction is recycled to the reactor and the bottom component is recycled to the extraction column.

As a preferred embodiment of the invention, in Step (4) the extractant is preferably water.

As a preferred embodiment of the invention, in Step (4) the molar ratio of the hydrogen chloride separation column component to the extractant is preferably 1:0.1-2.5.

As a preferred embodiment of the invention, in Step (4) the temperature of the extraction column is preferably 0-28° C., and the pressure is preferably 0.1-1.0 MPa.

The invention can produce a plurality of low-carbon foaming agent products by one set of plant through adjusting the process parameters, and can recover hydrogen fluoride from the crude product containing hydrogen fluoride and hydrogen chloride, the problem that a small amount of unseparated hydrogen chloride contained in the crude product cannot be recycled can be solved, and the recovered hydrogen fluoride can be returned to the reactor for continued use, thus reducing production costs. The hydrogen fluoride recovery column bottom component can be recycled as an extractant, which reduces the amount of alkaline used in subsequent alkaline washing, and significantly reduces the amount of alkaline washing wastewater. The advantages of simple process, environmental friendliness, high production efficiency, and low cost.

Compared with the prior art, the invention has the following advantages:

1. The process is simple and the operation flexibility is high. One set of plant can simultaneously produce products 1,1,1,3,3-pentafluoropropane, trans-1,3,3,3-tetrafluoropropene, cis-1,3,3,3-tetrafluoropropene, cis-1-chloro-3,3,3-trifluoropropene, and trans-1-chloro-3,3,3-trifluoropropene, and according to market conditions, the product proportion can be adjusted flexibly and the production can be organized flexibly.

2. The invention is environmentally friendly and the problem that a small amount of unseparated hydrogen chloride and hydrogen fluoride contained in the crude product cannot be recycled is solved. After the extraction, the hydrogen fluoride content in the product is 0.1% or below, and the recovered hydrogen fluoride can be returned to the reactor for further use, which reduces the production cost and the waste acid discharge. The hydrogen fluoride recovery column bottom component can be recycled as an extractant, which reduces the amount of alkaline used in subsequent alkaline washing and the amount of the extractant used in extraction, and significantly reduces the amount of alkaline washing wastewater.

3. The production efficiency is high, the gas phase reaction process adopted by the invention better solves the risk of the liquid phase reaction process, and the advantage that the catalyst has good activity and long service life is achieved.

4. The cost is low. The invention has mild operation conditions, low equipment investment, low energy consumption and large processing capacity, and is suitable for large-scale industrial production.

BRIEF DESCRIPTION OF THE DRAWING

FIG. 1 is a process flow diagram of the invention.

As shown in the FIGURE, 1 refers to reactor, 2 refers to recycle column, 3 refers to hydrogen chloride separation column, 4 refers to hydrogen fluoride recovery column, 5 refers to extraction column, 6 refers to alkaline washing column, 7 refers to first rectification column, 8 refers to second rectification column, 9 refers to third rectification column, and 10 refers to fourth rectification column.

DETAILED DESCRIPTION OF THE EMBODIMENTS

The process of the invention is as shown in FIG. 1. 1,1,1,3,3-pentachloropropane and hydrogen fluoride are preheated and then introduced into a reactor 1 to have a reaction in the presence of a catalyst to obtain a mixture containing 1,1,1,3,3-pentafluoropropane, trans-1,3,3,3-tetrafluoropropene, cis-1,3,3,3-tetrafluoropropene, cis-1-chloro-3,3,3-trifluoropropene, trans-1-chloro-3,3,3-trifluoropropene, hydrogen chloride, unconverted raw materials 1,1,1,3,3-pentachloropropane and hydrogen fluoride. The mixture obtained in the reactor 1 is introduced into a recycle column 2, and the recycle column 2 overhead fraction is a mixture containing 1,1,1,3,3-pentafluoropropane, trans-1,3,3,3-tetrafluoropropene, cis-1,3,3,3-tetrafluoropropene, cis-1-chloro-3,3,3-trifluoropropene, trans-1-chloro-3,3,3-trifluoropropene, hydrogen chloride and a small amount of hydrogen fluoride; the recycle column 2 bottom component is a mixture of 1,1,1,3,3-pentachloropropane and hydrogen fluoride, and the mixture of 1,1,1,3,3-pentachloropropane and hydrogen fluoride obtained at the bottom of the recycle column 2 is recycled to the reactor 1. The recycle column 2 overhead fraction is introduced into a hydrogen chloride separation column 3, and the hydrogen chloride separation column 3 overhead fraction is hydrogen chloride; the hydrogen chloride separation column 3 bottom component is a mixture containing 1,1,1,3,3-pentafluoropropane, trans-1,3, 3,3-tetrafluoropropene, cis-1,3,3,3-tetrafluoropropene, cis-1-chloro-3,3,3-trifluoropropene, trans-1-chloro-3,3,3-trifluoropropene and a small amount of hydrogen fluoride. The hydrogen chloride separation column 3 bottom component and the extractant are introduced into an extraction column 5 for extraction, and the extraction column 5 overhead component is a mixture of hydrogen fluoride and the extractant and is introduced into a hydrogen fluoride recovery column 4 for separation, and the hydrogen fluoride recovery column 4 overhead fraction is hydrogen fluoride and is recycled to the reactor 1, and the hydrogen fluoride recovery column 4 bottom component is the extractant and is recycled to an extraction column 5; and the hydrogen fluoride recovery column 4 bottom component is a mixture of 1,1,1,3,3-pentafluoropropane, trans-1,3,3,3-tetrafluoropropene, cis-1,3,3,3-tetrafluoropropene, cis-1-chloro-3,3,3-trifluoropropene and trans-1-chloro-3,3,3-trifluoropropene. The extraction column bottom component is introduced into an alkaline washing column 6 for alkaline washing, and then sequentially passes through a first rectification column 7, a second rectification column 8, a third rectification column 9, and a fourth rectification column 10 for rectification; a trans-1,3,3,3-tetrafluoropropene product is obtained at the overhead of the first rectification column 7, and a cis-1,3,3,3-tetrafluoropropene product is obtained at the overhead of the second rectification column 8, a 1,1,1,3,3-pentafluoropropane product is obtained at the overhead of the rectification column 9, a trans-1-chloro-3,3,3-trifluoropropene product is obtained at the overhead of the fourth rectification column 10, and a cis-1-chloro-3,3,3-trifluoropropene product is obtained at the bottom of the four rectification column.

The invention is further described in detail below by means of embodiments, but the invention is not limited to the embodiments described.

Embodiment 1

100 ml of a catalyst $Cr_2O_3$/In (load of In is 3 wt %) is loaded into a reactor, then the reactor is heated to 350° C., HF and nitrogen are introduced for activation, wherein the HF flow rate is 100 g/h, the nitrogen flow rate is 1.5 L/min, and the activation time is 50 hours.

Then, the feed reaction is started, and HF and R-240fa are preheated and then introduced into the reactor. The molar ratio of HF to R-240fa is 10:1, the reactor temperature is controlled to 150° C., the reaction pressure is 0.3 MPa, the space velocity is 100 $h^{-1}$, the molar ratio of the hydrogen chloride separation column bottom component to the extractant is 1:0.1, the temperature of the extraction column is 25° C., and the pressure of the extraction column is 0.1 MPa. The organic composition of the outlet product of the reactor is analyzed by sampling and gas chromatography, as shown in Table 1. Through analysis of samples from an extraction column bottom discharge pipeline, the hydrogen fluoride content is 0.1%.

TABLE 1

Outlet Organic Composition of the Reactor in Embodiment 1

| Component | | | | |
|---|---|---|---|---|
| R-1234ze(E) | R-1234ze(Z) | R-245fa | R-1233zd(E) | R-1233zd(Z) |
| Content (%) 1.74 | 0.43 | 0.17 | 81.39 | 15.76 |

Embodiment 2

100 ml of a catalyst $Cr_2O_3$/Zn (load of Zn is 3 wt %) is loaded into a reactor, then the reactor is heated to 350° C., HF and nitrogen are introduced for activation, wherein the HF flow rate is 100 g/h, the nitrogen flow rate is 1.5 L/min, and the activation time is 50 hours.

Then, the feed reaction is started, and HF and R-240fa are preheated and then introduced into the reactor. The molar ratio of HF to R-240fa is 15:1, the reactor temperature is controlled to 200° C., the reaction pressure is 0.5 MPa, the space velocity is 300 $h^{-1}$, the molar ratio of the hydrogen chloride separation column bottom component to the extractant is 1:1.0, the temperature of the extraction column is 15° C., and the pressure of the extraction column is 0.5 MPa. The organic composition of the outlet product of the reactor is analyzed by sampling and gas chromatography, as shown in Table 2. Through analysis of samples from an extraction column bottom discharge pipeline, the hydrogen fluoride content is 0.05%.

TABLE 2

Outlet Organic Composition of the Reactor in Embodiment 2

| Component | | | | |
|---|---|---|---|---|
| R-1234ze(E) | R-1234ze(Z) | R-245fa | R-1233zd(E) | R-1233zd(Z) |
| Content (%) 0.6 | 0.1 | 0.1 | 82.39 | 16.34 |

Embodiment 3

100 ml of a catalyst $Cr_2O_3$/In (load of In is 5 wt %) is loaded into a reactor, then the reactor is heated to 350° C., HF and nitrogen are introduced for activation, wherein the HF flow rate is 100 g/h, the nitrogen flow rate is 1.5 L/min, and the activation time is 50 hours.

Then, the feed reaction is started, and HF and R-240fa are preheated and then introduced into the reactor. The molar ratio of HF to R-240fa is 20:1, the reactor temperature is controlled to 250° C., the reaction pressure is 0.8 MPa, the space velocity is 500 $h^{-1}$, the molar ratio of the hydrogen chloride separation column bottom component to the extractant is 1:0.5, the temperature of the extraction column is 10° C., and the pressure of the extraction column is 0.3 MPa. The organic composition of the outlet product of the reactor is analyzed by sampling and gas chromatography, as shown in Table 3. Through analysis of samples from an extraction column bottom discharge pipeline, the hydrogen fluoride content is 0.08%.

TABLE 3

Outlet Organic Composition of the Reactor in Embodiment 3

| Component | | | | |
|---|---|---|---|---|
| R-1234ze(E) | R-1234ze(Z) | R-245fa | R-1233zd(E) | R-1233zd(Z) |
| Content (%) 4.11 | 7.89 | 83.12 | 2.05 | 2.83 |

Embodiment 4

100 ml of a catalyst $Cr_2O_3$/Zn (load of Zn is 7 wt %) is loaded into a reactor, then the reactor is heated to 350° C., HF and nitrogen are introduced for activation, wherein the HF flow rate is 100 g/h, the nitrogen flow rate is 1.5 L/min, and the activation time is 50 hours.

Then, the feed reaction is started, and HF and R-240fa are preheated and then introduced into the reactor. The molar ratio of HF to R-240fa is 25:1, the reactor temperature is controlled to 300° C., the reaction pressure is 1.0 MPa, the space velocity is 800 h$^{-1}$, the molar ratio of the hydrogen chloride separation column bottom component to the extractant is 1:2.0, the temperature of the extraction column is 0° C., and the pressure of the extraction column is 1.0 MPa. The organic composition of the outlet product of the reactor is analyzed by sampling and gas chromatography, as shown in Table 4. Through analysis of samples from an extraction column bottom discharge pipeline, the hydrogen fluoride content is 0.01%.

TABLE 4

Outlet Organic Composition of the Reactor in Embodiment 4

| | Component | | | | |
|---|---|---|---|---|---|
| | R-1234ze(E) | R-1234ze(Z) | R-245fa | R-1233zd(E) | R-1233zd(Z) |
| Content (%) | 0.97 | 2.03 | 96.5 | 0.2 | 0.3 |

Embodiment 5

100 ml of a catalyst Cr$_2$O$_3$/In (load of In is 7 wt %) is loaded into a reactor, then the reactor is heated to 350° C., HF and nitrogen are introduced for activation, wherein the HF flow rate is 100 g/h, the nitrogen flow rate is 1.5 L/min, and the activation time is 50 hours.

Then, the feed reaction is started, and HF and R-240fa are preheated and then introduced into the reactor. The molar ratio of HF to R-240fa is 30:1, the reactor temperature is controlled to 350° C., the reaction pressure is 1.5 MPa, the space velocity is 1000 h$^{-1}$, the molar ratio of the hydrogen chloride separation column bottom component to the extractant is 1:1.2, the temperature of the extraction column is 12° C., and the pressure of the extraction column is 0.5 MPa. The organic composition of the outlet product of the reactor is analyzed by sampling and gas chromatography, as shown in Table 5. Through analysis of samples from an extraction column bottom discharge pipeline, the hydrogen fluoride content is 0.07%.

TABLE 5

Outlet Organic Composition of the Reactor in Embodiment 5

| | Component | | | | |
|---|---|---|---|---|---|
| | R-1234ze(E) | R-1234ze(Z) | R-245fa | R-1233zd(E) | R-1233zd(Z) |
| Content (%) | 85.12 | 7.88 | 4.21 | 2.01 | 0.78 |

Embodiment 6

100 ml of a catalyst Cr$_2$O$_3$/Zn (load of Zn is 5 wt %) is loaded into a reactor, then the reactor is heated to 350° C., HF and nitrogen are introduced for activation, wherein the HF flow rate is 100 g/h, the nitrogen flow rate is 1.5 L/min, and the activation time is 50 hours.

Then, the feed reaction is started, and HF and R-240fa are preheated and then introduced into the reactor. The molar ratio of HF to R-240fa is 40:1, the reactor temperature is controlled to 400° C., the reaction pressure is 1.7 MPa, the space velocity is 900 h$^{-1}$, the molar ratio of the hydrogen chloride separation column bottom component to the extractant is 1:1.5, the temperature of the extraction column is 5° C., and the pressure of the extraction column is 0.7 MPa. The organic composition of the outlet product of the reactor is analyzed by sampling and gas chromatography, as shown in Table 6. Through analysis of samples from an extraction column bottom discharge pipeline, the hydrogen fluoride content is 0.03%.

TABLE 6

Outlet Organic Composition of the Reactor in Embodiment 6

| | Component | | | | |
|---|---|---|---|---|---|
| | R-1234ze(E) | R-1234ze(Z) | R-245fa | R-1233zd(E) | R-1233zd(Z) |
| Content (%) | 94.85 | 3.25 | 1.45 | 0.35 | 0.1 |

What is claimed is:

1. A method for co-producing low-carbon foaming agents, comprising following steps of:
   (1) preheating 1,1,1,3,3-pentachloropropane and hydrogen fluoride, introducing the 1,1,1,3,3-pentachloropropane and the hydrogen fluoride into a reactor, and reacting the 1,1,1,3,3-pentachloropropane and the hydrogen fluoride in the presence of a catalyst to obtain a reaction product, wherein a ratio of the 1,1,1,3,3-pentachloropropane and the hydrogen fluoride is 1:10-40, a temperature of the reaction is 150-400° C., a pressure of the reaction is 0.1-2.0 MPa, and a material space velocity of the reaction is 10-1000 h$^{-1}$;
   (2) introducing the reaction product obtained in the Step (1) into a recycle column to obtain a recycle column overhead fraction and a recycle column bottom component;
   (3) introducing the recycle column overhead fraction obtained in the Step (2) into a hydrogen chloride separation column to obtain a hydrogen chloride separation column overhead fraction and a hydrogen chloride separation column bottom component;
   (4) introducing the hydrogen chloride separation column bottom component obtained in the Step (3) and an extractant into an extraction column for extraction to obtain an extraction column overhead component and an extraction column bottom component; and
   (5) alkaline washing the extraction column bottom component obtained in the Step (4) and then rectifying to obtain following low-carbon foaming agent products: trans-1,3,3,3-tetrafluoropropene, cis-1,3,3,3-tetrafluoropropene, 1,1,1,3,3-pentafluoropropane, trans-1-chloro-3,3,3-trifluoropropene, and cis-1-chloro-3,3,3-trifluoropropene,
   wherein in the Step (1), the catalyst is Cr$_2$O$_3$/Zn, and wherein a load of Zn in the Cr$_2$O$_3$/Zn is 1-10 wt %.

2. The method for co-producing low-carbon foaming agents according to claim 1, wherein in the Step (2), the recycle column bottom component is recycled to the reactor.

3. The method for co-producing low-carbon foaming agents according to claim 1, wherein in the Step (4), the extraction column overhead component is introduced into a hydrogen fluoride recovery column for separation to obtain an overhead fraction and a bottom component, the overhead fraction is recycled to the reactor and the bottom component is recycled to the extraction column.

4. The method for co-producing low-carbon foaming agents according to claim 1, wherein in the Step (4), the extractant is water.

5. The method for co-producing low-carbon foaming agents according to claim 1, wherein in the Step (4), a molar ratio of the hydrogen chloride separation column bottom component to the extractant is 1:0.1-2.5.

6. The method for co-producing low-carbon foaming agents according to claim 1, wherein in the Step (4), a temperature of the extraction column is 0-28° C. and a pressure of the extraction column is 0.1-1.0 MPa.

\* \* \* \* \*